(12) United States Patent
Durance et al.

(10) Patent No.: US 8,718,113 B2
(45) Date of Patent: May 6, 2014

(54) APPARATUS AND METHOD FOR DEHYDRATING BIOLOGICAL MATERIALS

(75) Inventors: Timothy D. Durance, Vancouver (CA); Jun Fu, Port Coquitlam (CA); Parastoo Yaghmaee, Vancouver (CA); Robert L. Pike, Vancouver (CA); Vu Truong, San Jose, CA (US); Binh Pham, Mountain View, CA (US)

(73) Assignee: EnWave Corporation, Vancouver, British Columbia (CA)

( * ) Notice: Subject to any disclaimer, the term of this patent is extended or adjusted under 35 U.S.C. 154(b) by 866 days.

(21) Appl. No.: 12/677,974

(22) PCT Filed: Sep. 12, 2008

(86) PCT No.: PCT/CA2008/001615
§ 371 (c)(1),
(2), (4) Date: Oct. 22, 2010

(87) PCT Pub. No.: WO2009/033285
PCT Pub. Date: Mar. 19, 2009

(65) Prior Publication Data
US 2011/0027868 A1 Feb. 3, 2011

Related U.S. Application Data

(60) Provisional application No. 60/972,112, filed on Sep. 13, 2007.

(51) Int. Cl.
*C03B 5/02* (2006.01)
(52) U.S. Cl.
USPC .......................................................... 373/27
(58) Field of Classification Search
CPC ........ F26B 3/347; F26B 11/08; F26B 21/006; F26B 25/001; F26B 25/003; F26B 25/006; F26B 5/048; F26B 5/06; A23L 3/54; A61K 2039/545; A61K 39/0275; B01J 19/126; B01J 2219/1269; B01J 2219/1278; B01J 2219/1281; C12M 47/14; C12N 13/00; C12N 1/04; C12N 9/96; C13B 20/18; C13K 1/04; H05B 6/701

USPC ............ 373/27; 219/678, 679, 686, 687, 690, 219/695, 697, 702, 704, 710, 725, 728, 729, 219/730, 732, 734, 735, 736, 745, 746, 748, 219/750, 759, 762; 426/106, 107, 234, 237, 426/241, 243

See application file for complete search history.

(56) References Cited

U.S. PATENT DOCUMENTS 2,512,604 A 6/1950 Bierwirth
3,409,447 A * 11/1968 Jeppson ........................ 426/244

(Continued)

FOREIGN PATENT DOCUMENTS

| GB | 593806 | 10/1947 |
|---|---|---|
| GB | 608611 | 9/1948 |
| GB | 629979 | 10/1949 |
| WO | 97/38585 A1 | 10/1997 |
| WO | 01/26815 A1 | 4/2001 |
| WO | 2008/025258 A1 | 3/2008 |
| WO | 2008/134835 A1 | 11/2008 |

OTHER PUBLICATIONS

Search Report for co-pending PCT/CA2008/001615 listing relevant art cited by the International Searching Authority, Dated Jan. 7, 2009.

*Primary Examiner* — Dana Ross
*Assistant Examiner* — Joseph Iskra
(74) *Attorney, Agent, or Firm* — McKee, Voorhees & Sease

(57) ABSTRACT

An apparatus for dehydrating a liquid sample of biological material has a microwave waveguide that is open to the atmosphere. It has a microwave generator, means for introducing a container of the material into the waveguide, means for evacuating the container, means for rotating the container and means for removing the container from the waveguide. It can include means for moving the container through the waveguide and for sealing it. In a dehydration method, a container of the liquid sample is put into the open waveguide, evacuated, rotated at high speed and microwaved. The container of dehydrated material is then removed from the waveguide. The apparatus and method are particularly suitable for dehydrating vaccines.

14 Claims, 6 Drawing Sheets

(56) References Cited

U.S. PATENT DOCUMENTS

| | | |
|---|---|---|
| 4,616,427 A | 10/1986 | Takeuchi et al. |
| 4,856,203 A | 8/1989 | Wennerstrum |
| 5,117,564 A | 6/1992 | Taguchi et al. |
| 5,211,808 A | 5/1993 | Vilardi et al. |
| 5,338,409 A | 8/1994 | Heierli |
| 5,766,520 A | 6/1998 | Bronshtein |
| 6,225,611 B1 | 5/2001 | Pearcy et al. |
| 6,692,695 B1 | 2/2004 | Bronshtein et al. |
| 6,884,866 B2 | 4/2005 | Bronshtein et al. |

* cited by examiner

APPARATUS AND METHOD FOR DEHYDRATING BIOLOGICAL MATERIALS

FIELD OF THE INVENTION

The invention pertains to apparatuses and methods for microwave vacuum-drying of biological materials, such as vaccines, antibiotics, enzymes, proteins and microorganism cultures.

BACKGROUND OF THE INVENTION

Many biologically-active materials, such as vaccines, microbial cultures, etc., are dehydrated for purposes of storage. Methods used in the prior art include freeze-drying and air-drying methods such as spray-drying. Dehydration generally lowers the viability of the materials. Freeze-drying allows higher viability levels than air-drying but it requires long processing times and is expensive. It also causes some level of loss of viability in the dried materials.

It is also known in the art to dehydrate biological and other materials using a resonance chamber type of microwave vacuum dehydrator. This directs microwave energy into a vacuum chamber that serves as a resonance cavity for microwaves. However, particularly where the quantity of material being dried is relatively small, which is commonly the case with biomaterials, controlling the temperature of the material can be difficult. When microwaves are reflected within a resonance chamber, as the material dries the microwave energy output of the apparatus must be absorbed by less and less water and material in the sample. The mass of the material to be processed also has to be matched with the microwave power of the apparatus; quantities of material that are small relative to the microwave power of the apparatus may reach high temperatures when drying because of the abundance of microwave energy absorbed by the material.

SUMMARY OF THE INVENTION

The invention provides an apparatus and method for dehydrating a liquid sample of biological materials, in which the materials are dehydrated in an evacuated container which is in a microwave waveguide that is open to the atmosphere. Being open, the waveguide can be air-cooled to avoid overheating of the material. The likelihood of microwave arcing is reduced by reason of the field within the container being lower than in the open waveguide, due to attenuation of the radiation by the container. Since the dehydration is done under vacuum, i.e. at a pressure that is less than atmospheric pressure, the boiling point of water is reduced so the evaporation occurs at lower temperatures, minimizing damage to the biological activity of the material being dried. The container is rotated to control foaming of the material. More control of the temperature of the material can be achieved using the invention than using a resonance chamber type of microwave vacuum dehydrator. Very small quantities of material can be processed without overheating. Liquid samples of biological materials that can be processed by the invention include solutions and suspensions.

According to one embodiment of the invention, the apparatus comprises a microwave generator, a waveguide that is open to the atmosphere, means for introducing a container of biological material into the waveguide, means for applying a vacuum to the container, means for rotating the container, and means for removing the container from the waveguide.

The apparatus may optionally include means for removing a cap from the container, means for moving the container through the waveguide, and means for sealing the container.

According to another embodiment of the invention, the apparatus has a waveguide with an input end for the introduction of a microwave-transparent container of a biological material and a discharge end for removal of the container. The apparatus includes means for introducing the container into the input end, means for removing a cap from the container and means for applying a vacuum to the container. It includes means for moving the evacuated container through the microwave guide from the input end to the discharge end, means for rotating the evacuated container during the movement through the waveguide, means for replacing the cap onto the container and means for removing the container from the microwave guide at the discharge end. The apparatus may include a microwave absorbing sink at the end of the waveguide opposite to the generator.

According to another embodiment of the invention, there is provided a method for dehydrating biological materials. A container is provided holding a liquid sample of the biological material to be dehydrated, the container being transparent to microwave radiation. The container is put in a microwave waveguide that is open to the atmosphere. A vacuum is applied to the container. The evacuated container is rotated in the waveguide. Microwave radiation is applied to dehydrate the biological material. The container of dehydrated material is removed from the waveguide. Optionally, the container of dehydrated material is sealed before removal from the waveguide.

Where the container of material is capped before it is put into the microwave guide, the method includes removing the cap before applying microwave radiation.

According to another embodiment of the invention, there is provided a method for dehydrating a liquid sample of biological material, comprising the steps of providing a microwave-transparent container of the material, putting the container in a microwave waveguide that is open to the atmosphere, applying a vacuum to the container, rotating the container, moving the rotating, evacuated container through the waveguide while applying microwave radiation to dehydrate the material, optionally sealing the container of dehydrated material, and removing the container from the waveguide.

The invention accordingly produces containers of dehydrated biological material, which may be evacuated and sealed. It is particularly suitable for the production of vials of dehydrated vaccine, which can be reconstituted for use with a sterile saline solution.

These and other features of the invention will be apparent from the following description and drawings of the preferred embodiments.

DESCRIPTION OF THE PREFERRED EMBODIMENTS

The Dehydrating Apparatus

Figure 1:
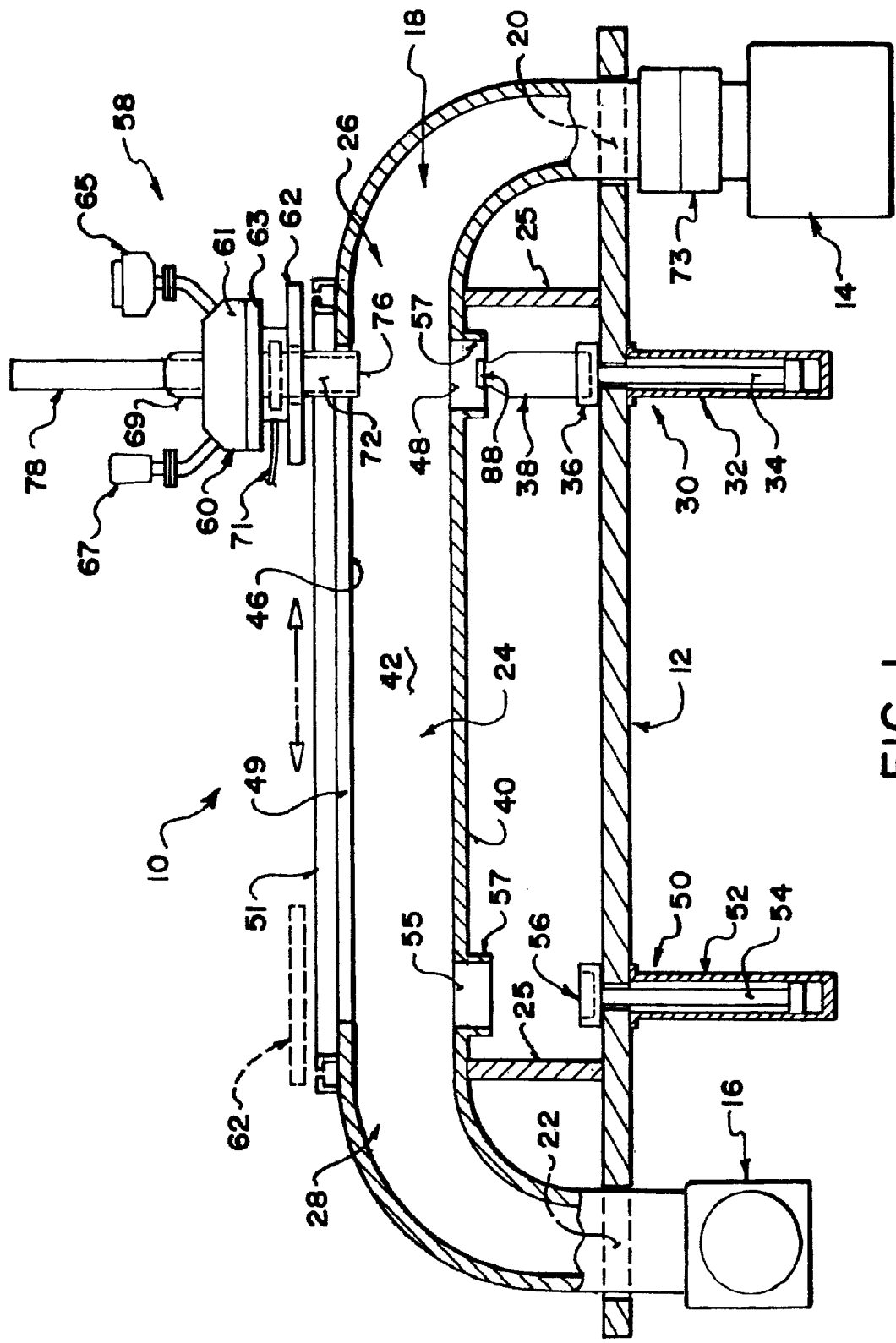
FIG. 1 is a side elevation view, partly in section, of an apparatus according to one embodiment of the invention.
Figure 2:
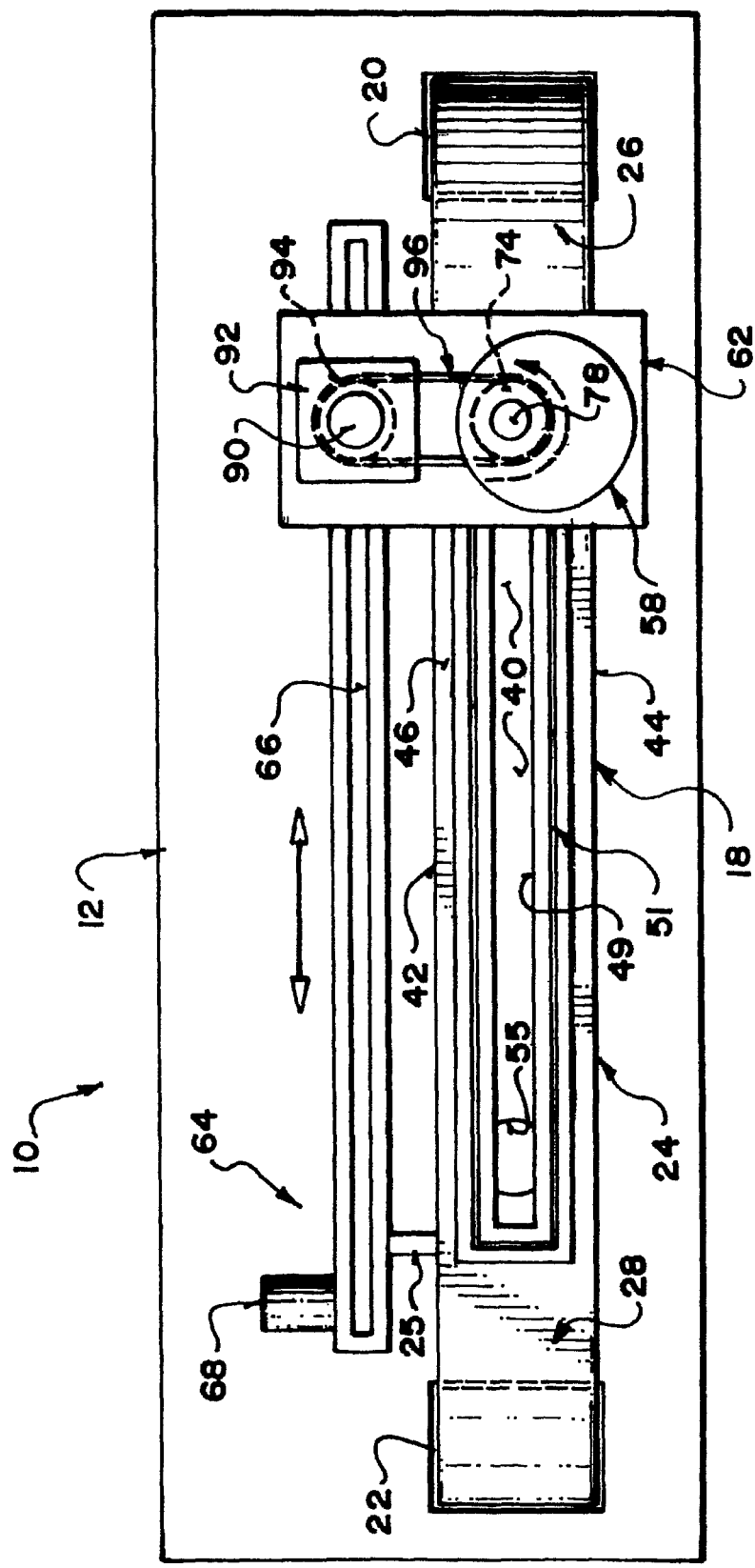
FIG. 2 is a top plan view thereof.

Referring to the drawings and in particular FIGS. 1 to 4 thereof, the dehydrating apparatus 10 has a support platform 12 with a microwave generator 14, a circulator 73 and a water sink 16 positioned below the platform 12. A microwave waveguide 18 above the platform extends between the circulator 73, and the water sink 16, passing through spaced-apart bores 20, 22 in the platform 12. The waveguide 18 is supported on the platform 12 by a frame 25. The waveguide 18 includes a longitudinally-extending section, referred to herein as the treatment section 24, through which the material to be dehydrated is moved, as described below.

The treatment section 24 has a bottom wall 40, side walls 42, 44 and an upper wall 46. A longitudinal slot 49 extends through the upper wall 46. The interior of the waveguide 18 is accordingly open to the atmosphere. The opening of the slot 49 is surrounded by a microwave choke 51, for reducing the escape of microwave radiation through the slot. There is a moveable cover (not shown) above the slot and choke to reduce the escape of radiation. The treatment section 24 has a product input end 26, into which the container of material to be dehydrated is introduced, and a product discharge end 28, from which the container of dehydrated material is removed. For purposes of the present description of the preferred embodiment, the container is a microwave-transparent vial 38 for containing, for example, a vaccine.

A vial-lifting mechanism 30 is affixed to the support platform 12 under the input end 26 of the treatment section 24 of the waveguide. The mechanism comprises an air cylinder 32 with a vial-lifting piston 34, mounted on the underside of the platform 12, with the piston 34 extending through a bore in the platform 12, and a vial-holding platform 36 on the upper end of the piston 34 for holding the vial 38 of material. The treatment section 24 of the waveguide 18 has a port 48 in its bottom wall 40 above the vial-holding platform 36, for entry of the vial 38 and the vial-lifting platform 36 into the treatment section 24.

A vial-lowering mechanism 50 is affixed to the support platform 12 under the product discharge end 28 of the treatment section 24. This mechanism is structurally the same as the vial-lifting mechanism 30, and comprises an air cylinder 52 with a vial-lowering piston 54, extending through a bore in the support platform 12, and a vial-holding platform 56 on the upper end of the piston 54. The treatment section 24 of the waveguide 18 has a port 55 in its bottom wall 40 above the vial-holding platform 56, for removal of the vial from the treatment section 24 after dehydration of the material. A tube 57 extends downwardly around the ports 48, 55 to reduce leakage of radiation from the waveguide.

A vial pickup head 58 provides for the transport of the vial 38 through the treatment section 24. The pickup head 58 has a body 60 affixed to a movable support platform 62. The platform 62 is arranged for movement along the treatment section 24 of the waveguide by a pickup head moving mechanism 64. This mechanism comprises a belt drive 66 supported on the frame 25, parallel to the treatment section 24, and driven by a motor 68. The moveable support platform 62 is affixed to the belt drive 66 for movement thereon, such that actuation of the belt drive 66 moves the pickup head 58 along the length of the treatment section 24. The cover for the waveguide slot can be affixed to, or be an extension of, the support platform 62.

The vial pickup head 58, as best seen in FIG. 1, has a body 60 with an upper part 61 and a base part 63. The upper part 61 has ports which lead respectively to a condenser 65, a temperature sensor 67 and a vacuum sensor 69 (omitted from FIGS. 2 to 4 for clarity). The condenser 65 contributes to the condensation of moisture given off from the material during dehydration. The temperature sensor 67 and vacuum sensor 69 respectively measure the temperature and pressure within the vial. The upper part 61 is rotatable on the base part 63 of the pickup head body 60 about a vertical axis, in order to permit the vertical alignment of the respective sensors with the vial, when a measurement is desired.

The body 60 of the pickup head has a vacuum cavity 70 therein in the form of a cylindrical bore. A vacuum source, condenser and vacuum line (not shown) are connected to a vacuum port 71 in the base part 63 of body 60 of the vial pickup head to provide for the evacuation of the vacuum cavity 70 and removal and condensation of moisture from the material. A vial pickup sleeve 72 is mounted in the vacuum cavity 70 for rotation about its longitudinal axis and is positioned with its upper portion in the vacuum cavity 70 and its lower portion extending through a bore in the pickup head support platform 62 and through the longitudinal slot 49 in the upper wall 46. The sleeve 72 thus extends into the treatment section 24 of the waveguide 18. A pulley 74 is provided on the outside of the pickup sleeve 72 above the level of the support platform 62, for rotation of the pickup sleeve 72 and the vial 38, as discussed below. A sealing surface 76 is provided at the bottom edge of the sleeve 72 for airtight sealing engagement with the vial 38.

An air cylinder 78 is affixed to the upper part 61 of the pickup head body 60. It has a piston 80 which extends through a bore 82 in the upper end of the body 60 and into the pickup sleeve 72. A cap holder 84 at the bottom end of the piston 80 has a circumferential flange 86 shaped and adapted to engage and hold a cap 88 of the vial 38.

A drive motor 90 is mounted on a stand 92 on the pickup head support platform 62 and has a pulley 94 positioned in a space between the underside of the stand 92 and the upper side of the platform 62, with a drivebelt 96 which extends into the body 60 of the vial pickup head 58 through a slot 98 to engage the pulley 74 on the pickup sleeve 72. Actuation of the drive motor 90 moves the belt 96, rotating the pickup sleeve 72.

It will be understood that the apparatus 10 also includes appropriate air lines and controls to actuate the air cylinders, a vacuum line and controls to evacuate the vacuum chamber 70, and controls to operate the drive motors.

The Methods of Dehydrating

At the start of a cycle of operation of the dehydrating apparatus 10, the vial-lifting piston 34 and the vial-lowering piston 54 are both in their retracted positions, such that the vial-holding platforms 36, 56 are on the support platform 12. The pickup head piston 80 is also in its retracted position, such that the cap holder 84 is in its raised position within the body 60 of the pickup head 58. The pickup head support platform 62 is at the inlet end 26 of the treatment section 24 of the waveguide 18, with the pickup head 58 vertically aligned with the vial entry port 48. The vial 38 with a liquid sample of material to be dehydrated, e.g. a vaccine suspension, covered by a cap 88 and at atmospheric pressure, is placed on the vial-holding platform 36.

Figure 3:
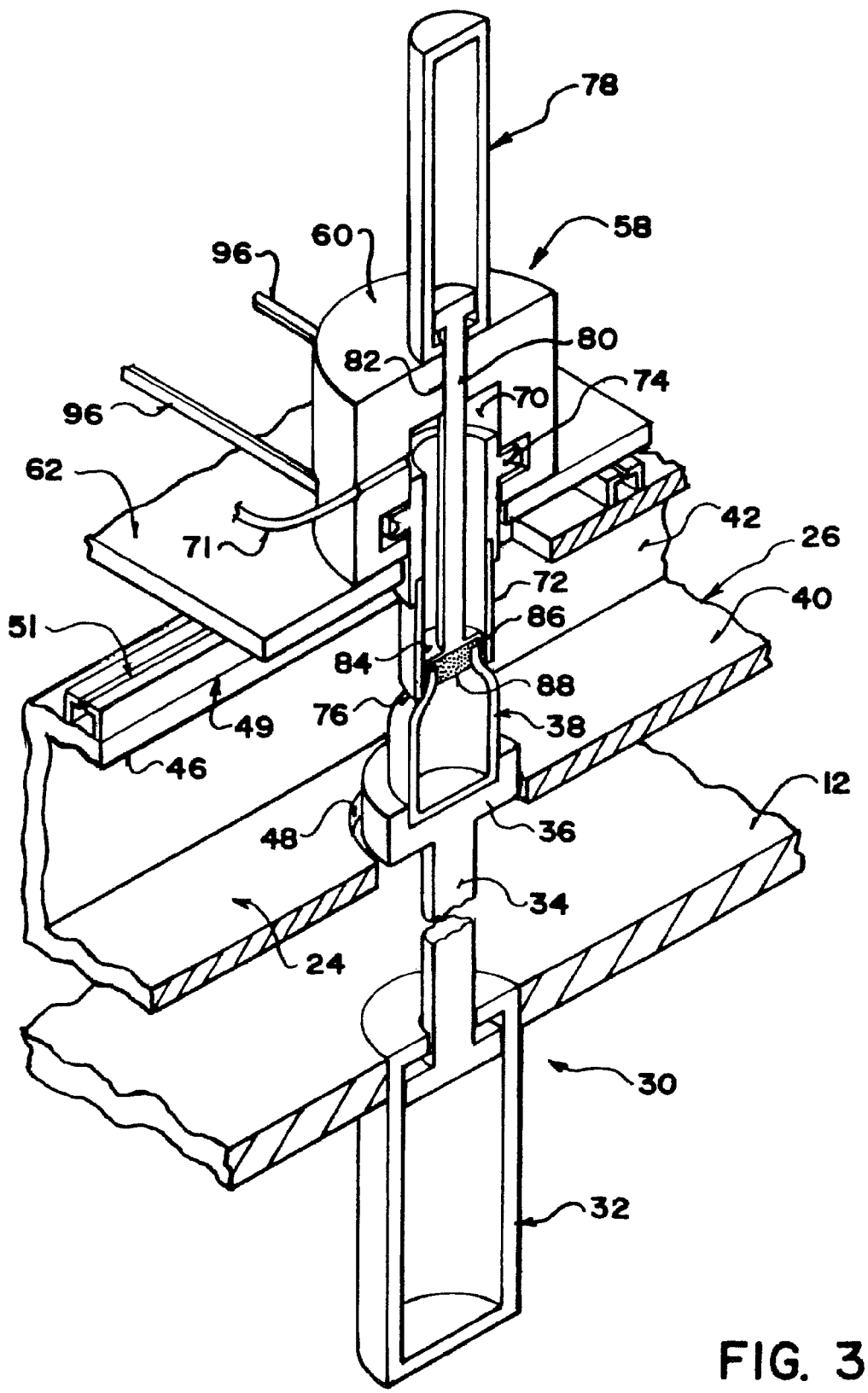
FIG. 3 is a cross-sectional view of part of the apparatus at the input end, prior to removal of the cap from the vial.

The vial-lifting cylinder 32 is actuated to raise the piston 34 and the vial-holding platform 36, lifting the vial 38 through the vial entry port 48 into the treatment section 24 of the waveguide, until the shoulder of the vial abuts the sealing surface 76 at the lower end of the vial pickup sleeve 72. The pickup head air cylinder 78 is then actuated, to lower the pickup head piston 80 and cap holder 84 to engage the cap 88 of the vial. This position of the apparatus is shown in FIG. 3. A vacuum is then applied to the vacuum chamber 70 by means of the vacuum source and line. Absolute pressures in the vacuum chamber in the range of 4 to 40 mm of mercury are suitable for most materials.

The pickup head air cylinder 78 is then actuated, lifting the cap holder 84 and removing the cap 88 from the vial 38. This removal is facilitated by the pressure differential between the inside of the vial, which is at atmospheric pressure, and the partial vacuum of the vacuum chamber 70 and pickup sleeve 72. The cap removal causes a vacuum to be applied to the vial 38. The vacuum applied through the pickup sleeve 72 causes a seal between the vial and the pickup sleeve 72 at the sealing surface 76, permitting the vial to be held securely by the pickup sleeve 72. The vial-lifting cylinder 32 is then actuated to lower the vial-lifting piston 34, withdrawing the vial-holding platform 36 from the waveguide 18.

The pickup drive motor 90 is then actuated, driving the pulley 74 on the pickup sleeve 72, causing the sleeve, and with it the vial 38, to rotate at high speed, e.g. 300 to 2,000 rpm, about its longitudinal axis. This rotation causes the material in the vial to form a film on the side walls of the vial, due to centrifugal force. It is believed that the formation of such film of material on the vial walls, being between the microwave field and the vacuum inside the vial, reduces arcing in the vial during the dehydration process. The high speed rotation also controls foaming of the material. The rotation speed is accordingly to be sufficient to form a film and control foaming. Rotation can additionally be considered as evening out the microwave field experienced by the material, though slow speed rotation, e.g. 10 rpm, would be sufficient for that purpose.

The microwave generator 14 is then actuated, causing microwave energy to travel through the waveguide 18 to the water sink 16. The circulator 73 prevents microwave energy from re-entering the generator. The belt drive motor 68 is actuated, to move the belt drive 66 and accordingly the pickup head support platform 62. The direction of movement of the support platform 62 is towards the discharge end 28 of the treatment section 24. The vial 38 remains evacuated and spinning as it is moved towards the discharge end 28. The heating of the biological material by the microwave energy causes evaporation of the water and dehydration of the material. If desired, the pressure and temperature in the vial can be measured during the dehydration process by means of the sensors 69, 67.

Figure 4:
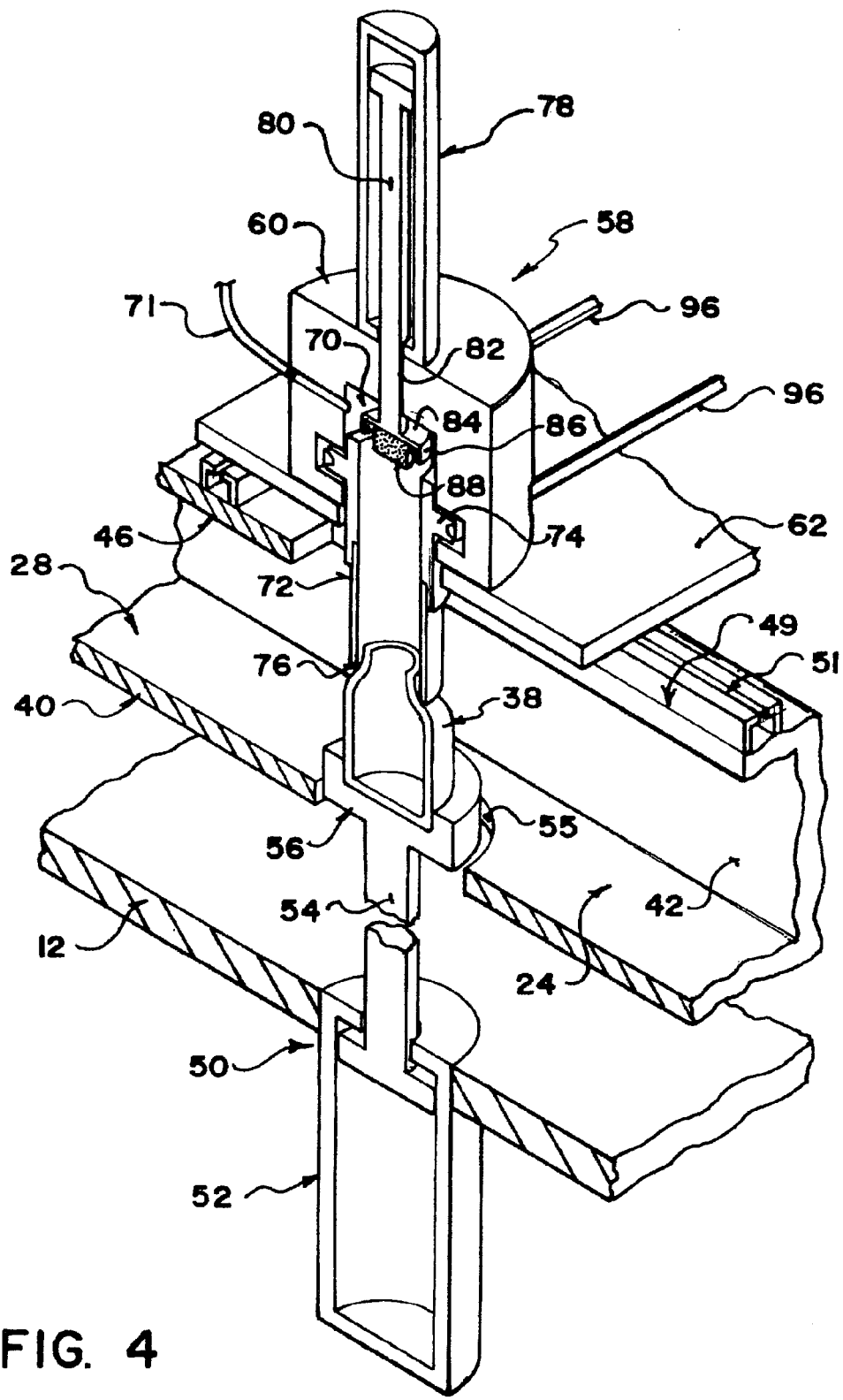
FIG. 4 is a cross-sectional view of part of the apparatus at the discharge end, prior to replacement of the cap on the vial.

At the discharge end 28, the vial 38 is brought into alignment with the vial removal port 55 in the bottom wall 40 of the treatment section 24 and the belt drive motor 68 is stopped. The microwave generator 14 is deactivated and the pickup drive motor 90 is turned off to stop the rotation of the vial 38. The air cylinder 52 is actuated to raise the vial-lowering piston 54, extending the vial-holding platform 56 through the port 55 into the treatment section 24 of the microwave guide so it engages the bottom of the vial 38. This position is shown in FIG. 4. The pickup head air cylinder 78 is actuated to lower the pickup head piston 80, pushing the cap 88 back onto the vial 38. The vacuum in the vacuum chamber 70 is then released. This breaks the seal between the pickup sleeve 72 and the vial 38 at the sealing surface 76, releasing the vial from the grip of the sleeve. The release of vacuum also results in a pressure differential between the inside of the vial, which is at reduced pressure, and the vacuum chamber 70 and pickup sleeve 72, which are now at atmospheric pressure. The pickup head air cylinder 78 is then actuated, to lift the piston 80 and the cap holder 84. Due to the pressure differential, the reduced pressure in the vial holds the cap 88 in place on the vial 38 as the cap holder 84 is retracted. The air cylinder 52 is then actuated to lower the vial-holding platform 56, and with it the vial 38, withdrawing the vial from the waveguide 18. The vial can then be manually removed from the apparatus 10. It is a vacuum sealed, capped vial containing dehydrated material.

To return the apparatus to the starting condition for processing of a further vial of material, the drive motor 68 is actuated to return the pickup head 58 to the input end 26 of the treatment section 24.

Figure 5:
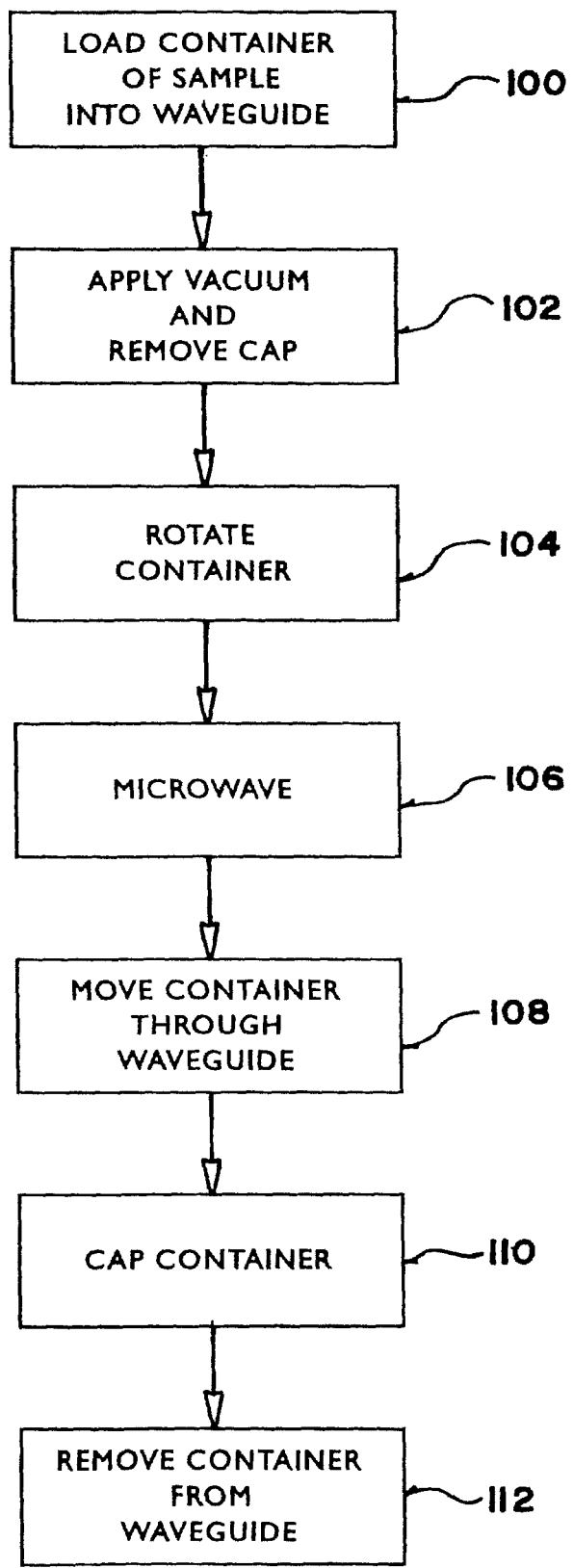
FIGS. 5 and 6 are flow diagrams of methods of dehydration according to the invention.

The foregoing method can be understood in general terms as comprising the following steps, as illustrated in the flow diagram of FIG. 5. In step 100, the capped vial of biological material is loaded into the waveguide. In step 102, the cap is removed and vacuum is applied to the vial. In step 104, the vial is rotated. In step 106, microwave energy is directed through the waveguide. In step 108, the rotating vial is moved through the waveguide to the outlet end. In step 110, the vial is capped. In step 112 the evacuated vial of dehydrated material is removed from the waveguide.

Instead of capping the vial of dehydrated material in the waveguide, the vial may alternatively be removed uncapped. Capping would then be done subsequently, after removal of the vial from the apparatus.

Figure 6:
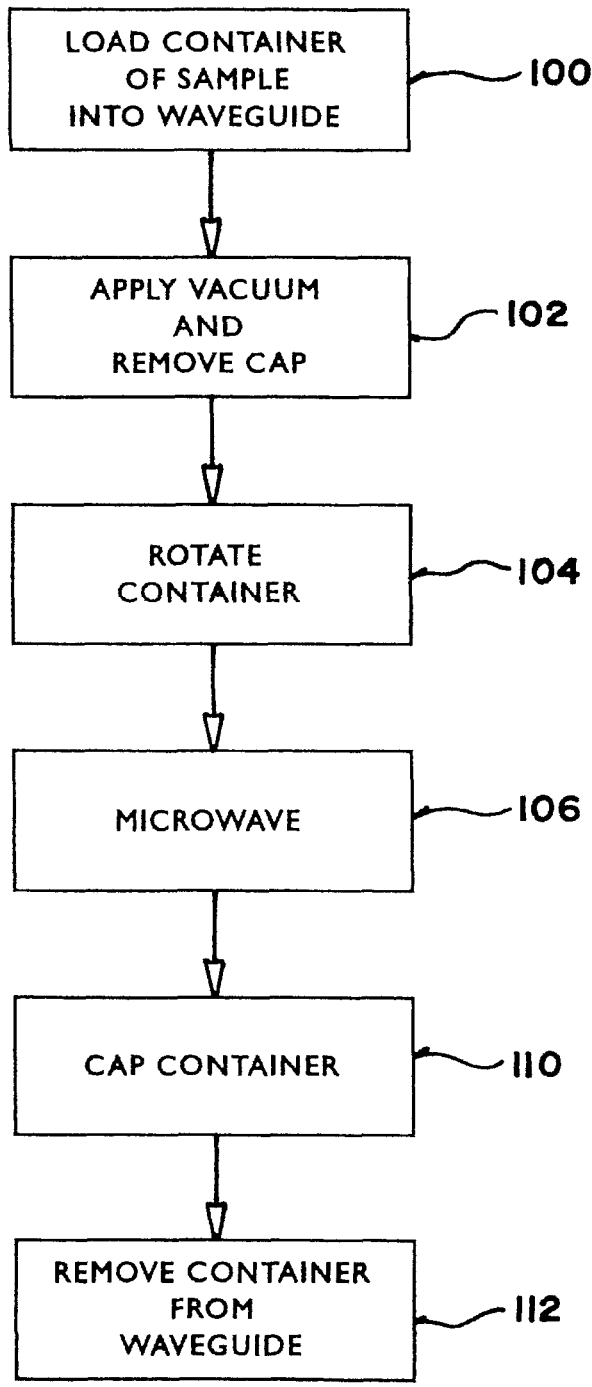

Dehydration of biological materials can also be achieved without the step of moving the rotating vial through the waveguide. It is necessary in this method that the intensity of microwave energy at the fixed position of the vial in the waveguide be appropriate for the sample. The steps of this method comprise steps 100, 102, 104, 106, 110 and 112, as illustrated in FIG. 6.

Example 1

An apparatus according to the invention has a microwave generator having a power output of 900 watts, a water sink and a microwave guide extending between them. The guide has a treatment section approximately 33 cm long, with a channel that is rectangular in cross-section approximately 5.25 cm high and 10.9 cm wide. The slot in the upper wall of the treatment section is approximately 2.8 cm wide and is surrounded by a microwave choke. A 0.5 ml sample of a vaccine consisting of live attenuated bacteria is placed in a 10 ml capped borosilicate glass vial. The vial is introduced into the input end of the treatment section of the microwave guide. The pickup head uncaps and evacuates the vial to an absolute pressure of 5 mm of mercury, rotates it at 500 rpm and moves it to the discharge end of the treatment section of the guide while microwave radiation is transmitted through the guide. The pickup head then caps the evacuated vial and the vial is removed from the guide. The dwell time of the vial in the guide for dehydration is approximately 300 seconds. The dehydrated vaccine forms a film on the inside walls of the vial and is reconstituted with a sterile saline solution.

Example 2

*Lactobacillus salivarius* was mixed with various protecting agents according to formulations 1 to 3.

| Formula No. | Composition |
| --- | --- |
| 1 | Skim milk powder (10% w/v) + 2.5% (w/v) glycerol |
| 2 | Bovine serum albumin (10% w/v) + 2.5% (w/v) glycerol |
| 3 | Lactose (10% w/v) + 2.5% (w/v) glycerol |

The samples were dried using the apparatus of the invention by microwaving at 750 W for 6 minutes followed by microwaving at 200 W for 6 minutes, at a pressure of 5 mm of mercury and a rotation speed of 900 rpm. Samples were also dried in a freeze dryer as a control.

The viability of the dehydrated samples was determined by plating serial dilutions on petrifilms. Plates were incubated anaerobically, at 37° C. for 48 hours. The results are reported as percent of colony-forming units that survive dehydration.

| Formula No. | Microwave Drying | Control (Freeze-dried) |
| --- | --- | --- |
| 1 | 52.90 ± 12.6% | 39.89 ± 17.2% |
| 2 | 50.47 ± 12.6% | 51.05 ± 21.8% |
| 3 | 56.59 ± 12.0% | 65.66 ± 18.0% |

Example 3

Samples of *Salmonella typhimurium* 21a mixed with a complex medium (trehalose, glycerol, gelatin, methionine and $KH_2PO_4$, pH 7.0) were dried in triplicate using the apparatus of the invention, with a rotation speed of 1,000 rpm, vacuum set at 5 mm of mercury, and a drying time of 2,100 sec. The power level was adjusted in a way that the temperature of the sample did not exceed 38° C. The viability of the dehydrated samples was 8.1±3.0%. The moisture content was 5.4±0.8%.

Although the invention has been described in terms of various embodiments, it is not intended that the invention be limited to these embodiments. Various modifications within the scope of the invention will be apparent to those skilled in the art. For example, the containers may be of various sizes, larger or smaller than those described. As another example, the vials being introduced into the waveguide are not necessarily already capped. They may be filled immediately before being fed to the waveguide and loaded into it uncapped. In such case, the apparatus would include a cap-feeding mechanism so that processed vials can be sealed with caps. The scope of the invention is defined by the claims that follow.

| List of Components in the Drawings | |
| --- | --- |
| 10 | dehydrating apparatus |
| 12 | support platform |
| 14 | microwave generator |
| 16 | water sink |
| 18 | microwave waveguide |
| 20, 22 | bores in platform 12 for the waveguide |
| 24 | treatment section of the waveguide |
| 25 | frame |
| 26 | input end of treatment section |
| 28 | discharge end of treatment section |
| 30 | vial-lifting mechanism |
| 32 | vial-lifting air cylinder |
| 34 | vial-lifting piston |
| 36 | vial-holding platform |
| 38 | vial |
| 40 | bottom wall of treatment section |
| 42, 44 | side walls of treatment section |
| 46 | upper wall of treatment section |
| 48 | vial entry port |
| 49 | longitudinal slot in upper wall of treatment section |
| 50 | vial-lowering mechanism |
| 51 | microwave choke |
| 52 | vial-lowering air cylinder |
| 54 | vial-lowering piston |
| 55 | vial-removal port |
| 56 | vial-holding platform |
| 57 | tubes below vial ports |
| 58 | vial-pickup head |
| 60 | body of vial-pickup head |
| 61 | swivelling part of 60 |
| 62 | pickup head support platform |
| 63 | base part of 60 |
| 64 | pickup head moving mechanism |
| 65 | condenser |
| 66 | belt drive |
| 67 | temperature sensor |
| 68 | belt drive motor |
| 69 | vacuum sensor |
| 70 | vacuum cavity in vial-pickup head |
| 71 | vacuum port in body 60 |
| 72 | vial-pickup sleeve |
| 73 | circulator |
| 74 | pulley on vial-pickup sleeve |
| 76 | sealing surface of pickup sleeve |
| 78 | air cylinder on pickup head |
| 80 | piston for air cylinder on pickup head |
| 82 | bore in top of body 60 |
| 84 | cap holder |
| 86 | flange on cap holder |
| 88 | cap of vial |
| 90 | drive motor on pickup head support platform |
| 92 | stand on pickup head support platform |
| 94 | pulley on drive motor 90 |
| 96 | drivebelt for pickup head |

What is claimed is:

1. An apparatus for dehydrating a liquid sample of biological material, comprising:
   (a) a microwave generator;
   (b) a waveguide to direct microwave radiation from the generator, the waveguide being open to the atmosphere;
   (c) means for introducing a microwave-transparent container of the material into the waveguide;
   (d) means for applying a vacuum to the container;
   (e) means for rotating the container; and
   (f) means for removing the container from the waveguide.

2. An apparatus according to claim 1, further comprising means for moving the container through the waveguide from an input end to a discharge end of the waveguide.

3. An apparatus according to claim 1, further comprising means for sealing the container of dehydrated material.

4. An apparatus according to claim 1, further comprising means for removing a cap from the container.

5. An apparatus according to claim 1, further comprising a microwave sink at an end of the waveguide remote from the generator.

6. An apparatus according to claim 1, wherein the means for introducing the container into the waveguide comprises a container-lifting mechanism having a piston for lifting the container through a port in a lower side of the waveguide.

7. An apparatus according to claim 1, wherein the means for removing the container from the waveguide comprises a container-lowering mechanism having a piston for lowering the container through a port in a lower side of the waveguide.

8. An apparatus according to claim 1, wherein the means for applying a vacuum to the container comprises a container pickup head operatively connected to a vacuum source.

9. An apparatus according to claim 1, wherein the means for rotating the container comprises a motor operatively connected to a rotatable sleeve.

10. An apparatus according to claim 2, wherein the means for moving the container through the waveguide comprises a moveable support platform for a container pickup head, the support platform being connected to a drivebelt arranged generally parallel to the waveguide.

11. An apparatus according to claim 4, wherein the means for removing a cap comprises a capholder operatively connected to a piston, the capholder being movable by the piston from a lower position to remove or replace the cap on the container and an upper position to hold the cap off the container.

12. An apparatus according to claim 1, further comprising a condenser operatively connected to the means for applying a vacuum.

13. An apparatus according to claim 8, wherein the container pickup head comprises a base portion and an upper portion rotatable on the base portion, the upper portion having at least one of a temperature sensor and a pressure sensor.

14. An apparatus according to claim 1, wherein the waveguide has a longitudinal slot in an upper wall of the waveguide.

* * * * *